United States Patent [19]

Loev et al.

[11] Patent Number: 4,595,696
[45] Date of Patent: Jun. 17, 1986

[54] POLYENE COMPOUNDS USEFUL IN THE TREATMENT OF ALLERGIC RESPONSES

[75] Inventors: Bernard Loev, Scarsdale; Wan-Kit Chan, Yorktown Heights, both of N.Y.

[73] Assignee: USV Pharmaceutical Corp., Tarrytown, N.Y.

[21] Appl. No.: 775,870

[22] Filed: Sep. 13, 1985

[51] Int. Cl.$^4$ .................. A61K 31/21; A61K 31/24
[52] U.S. Cl. .................................. 514/513; 514/540
[58] Field of Search .................. 514/513, 540, 541

[56] References Cited

U.S. PATENT DOCUMENTS 4,400,390 8/1983 Pittet et al. .................. 514/513

Primary Examiner—Stanley J. Friedman

[57] ABSTRACT

Polyene compounds represented by the general formula

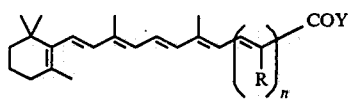

where
R=H or lower alkyl group of from 1 to 5 carbon atoms

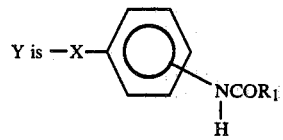

n is 0–1
x is O or S; and
$R_1$=an alkyl group of from 1 to 5 carbon atoms; and the pharmaceutically acceptable salts thereof.

and the pharmaceutically acceptable salts thereof.

The foregoing compounds have been found to be effective in regulating the formation of lipoxygenese and as such possess therapeutic value in the treatment of inflammatory conditions and allergic responses.

2 Claims, No Drawings

POLYENE COMPOUNDS USEFUL IN THE TREATMENT OF ALLERGIC RESPONSES

BACKGROUND OF THE INVENTION

The present invention relates to polyene compounds and more particularly to phenolic esters of polyolefinic carboxylic acids derived from such polyolefinic intermediates as retinoic acid or retinal (3,7-dimethyl-9-(2,6,6-trimethyl-1-cyclohexen-1-yl)-2,4,6,8-nonatetraenal; vitamin A aldehyde) which possesses the structure

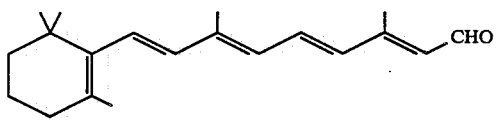

A synthesis of retinal from beta-ionone and propargyl halide is described in U.S. Pat. No. 3,060,229.

Other prior art publications include: U.S. Pat. No. 4,534,979 describes certain polyene compounds for the treatment of psoriasis and allergic responses; German Offen. No. 2,202,689 (1972) describes the compound

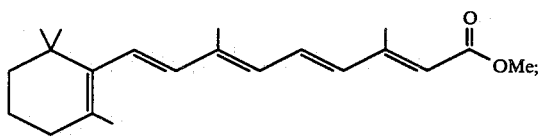

German Offen. No. 2,354,792 (1974) describes

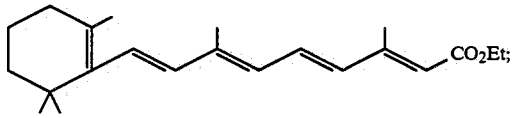

Japanese Pat. No. 74 76,048 (1975) describes

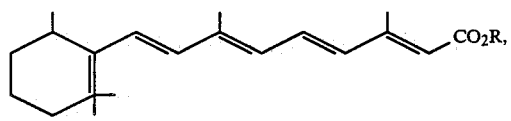

wherein R=$C_{5-20}$ hydrocarbon residue;
So. African Pat. No. 71 00,145 (1971) describes

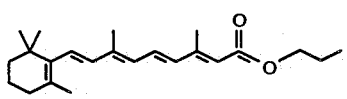

for treating acne or psoriasis; and Belg. Pat. No. 847,942 (1977) describes all-transretinoic acid esters and amides of the formula

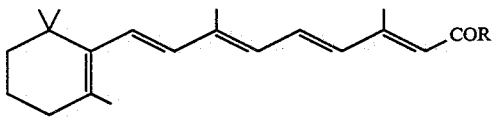

where R=2-cyclohexylethoxy, $MeO_2C(CH_2)_{10}O$, $HO(CH_2)_4O$, cholesteryl, 3—$CH_2$:$CHC_6H_4CH_2O$, 4—$CH_2$:$CHC_6H_4$ $CH_2O$, 4-$BrC_6H_4CH_2O$, $OCH_2COR^1$, NHPr, $NHCMe_3$, $NHCMe_2CH_2CMe_3$, morpholino, 4—$HOC_6H_4NH$, 4,2—$MeO_2C(HO)C_6H_3NH$, 3,4—$(MeO)_2C_6H_3CH_2CH_2NH$, 2-benzothiazolylamino, 1-imidazoylyl, 2-nicotinoylhydrazino, 1-benzotriazolyl, 1,2,4-triazol-1-yl, β-ionone hydrazono N-cyclohexylaminocarbonyl-N-cyclohexylamino.

SUMMARY OF THE INVENTION

The present invention is directed to polyene compounds of the general formula

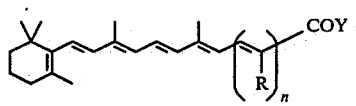

where
R=H or lower alkyl group of from 1 to 5 carbon atoms

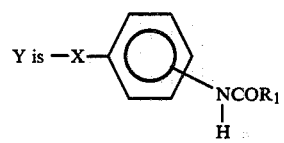

n is 0-1
x is 0 or S; and
$R_1$=an alkyl group of from 1 to 5 carbon atoms; and the pharmaceutically acceptable salts thereof.

DETAILED DESCRIPTION OF THE INVENTION

The compounds of this invention can be prepared from known polyolefinic materials, e.g., polyene acids, employing known synthetic procedures or from analogous polyolefinic compounds which can be prepared in accordance with methods known by those skilled in the art.

The compounds of this invention can also be prepared by reaction of polyenoic acids with appropriate phenols in the presence of a dehydrating agent, such as dicyclohexylcarbodiimide or 1-cyclohexyl-3-(2-morpholinoethyl)carbodiimide metha-p-toluenesulfonate.

Another general method of preparation uses appropriate reagents to activate polyenoic acids before their treatment with phenolic compounds. Examples of such activating reagents are: acetic anhydride, boron trifluoride, oxalyl chloride, phosphorus trichloride, thionyl chloride or other reagents known to be useful in ester formation.

The compounds of this invention can also be prepared by partial reduction of corresponding compounds containing acetylenic in lieu of ethylenic bonds.

The preferred methods of synthesizing the compounds of the invention are described in the Examples that follow.

EXAMPLE 1

4-Acetamidophenyl Retinoate

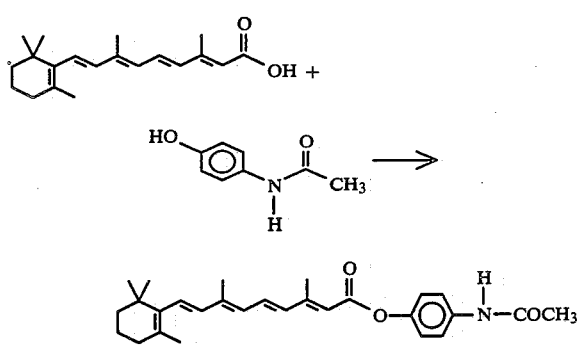

A solution of retinoic acid (2 g, 6.65 mmol) and 4-acetamidophenol (1.2 g, 8 mmol) in 40 ml of tetrahydrofuran (THF) was stirred in an ice bath under nitrogen and a solution of trifluoracetate (1.4 ml) in 5 ml of THF was added dropwise. The mixture was stirred at room temperature for 24 hours and concentrated in vacuo. The residue was diluted with methylene chloride and washed with aqueous NaHCO$_3$ solution and brine. After drying with Na$_2$SO$_4$, the organic solution was concentrated in vacuo to give a yellow powder. Crystallization from ethyl acetate afforded 2.7 g of title compound as yellow crystals: mp 213°–214° C. MS(EI): 433(M+).

EXAMPLE 2

3-Acetamidophenyl Retinoate

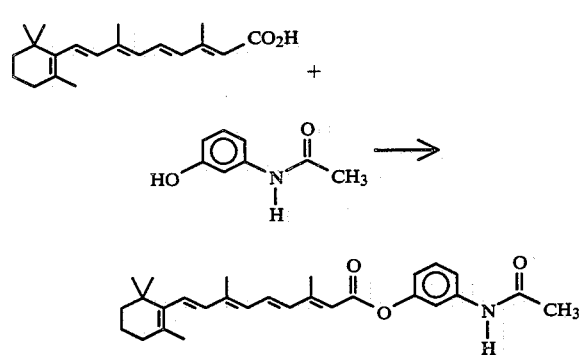

In a manner similar to Example 1, retinoic acid (1 g, 33 mmol) was condensed with 3-acetamidophenol to give, after crystallization from ethyl acetate/ether, 0.9 g of 3-acetamidophenyl retinoate as yellow crystals, mp 171°–173° C. MS (EI): 433 (M+), 283,175.

EXAMPLE 3

Retinoic Acid 4-Acetamidophenyl Thioester

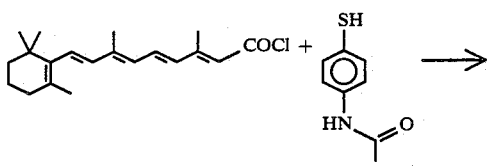

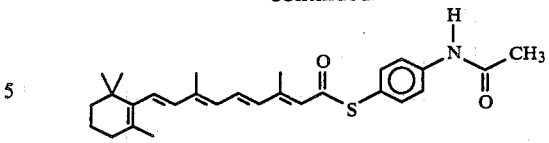

Retinoyl chloride was prepared from 1 g (3.3 mmol) of retinoic acid with PCl$_3$ in 15 ml of anhydrous toluene and reacted with 4-acetamidothiophenol (0.5 g, 2.8 mmol) in the presence of pyridine in 8 ml of THF. The reaction mixture was stirred under nitrogen at room temperature for 6 hours and diluted with chloroform. The organic solution was washed with 5% aqueous NaHCO$_3$ and water. After drying (Na$_2$SO$_4$), the solvent was removed in vacuo to give a yellow foam. Crystallization from chloroform/petroleum ether afforded the title compound as yellow crystals: mp 115° C. (decomp.): MS (EI): 449(M+) 282, 167, 159, 125; UV(-MeOH) λmax. 286 nm, 258 nm.

EXAMPLE 4

4-Acetamidophenyl 5,9-dimethyl-11-(2,6,6-trimethyl-1-cyclohexen-1-yl)-2,4,6,8,10-undecapentaenoate

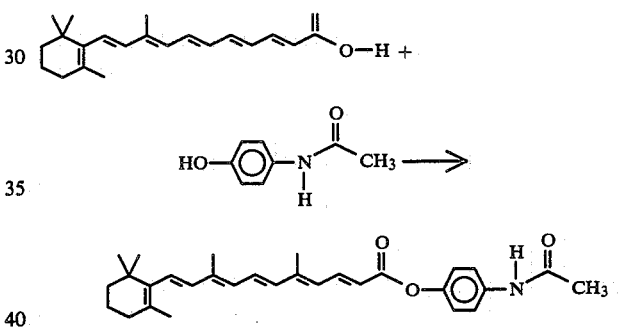

A solution of 5,9-dimethyl-11-(2,6,6-trimethyl-1-cyclohexen-1-yl)-2,4,6,8,10-undecapentaenoic acid (0.5 g. 1.5 mmol) and 4-acetamidophenol (1.2 g, 8 mmol) in 40 ml of tetrahydrofuran (THF) was stirred in an ice bath under nitrogen and a solution of trifluroacetate (1.4 ml) in 5 ml of THF was added dropwise. The mixture was stirred at room temperature for 24 hours and concentrated in vacuo. The residue was diluted with methylene chloride and washed with aqueous NaHCO$_3$ solution and brine. After drying with Na$_2$SO$_4$, the organic solution was concentrated in vacuo to give orange powders. Crystallization from ethyl acetate afforded 0.55 g. of the title compound as orange colored crystals. mp 219°–222° C., MS (EI): 459 (m+), 309, 291, 109; UV(-MeOH) λmax. 394 nm, 245 nm.

Compounds of the present invention were found to have potent activity in regulating the formation of lipoxygenase and as such possess therapeutic value in the treatment of inflammatory conditions and allergic responses such as anaphylaxis and asthma.

Lipoxygenases in mammals have been found in the lung, platelets, and white cells. They are enzymes capable of oxidizing arachidonic acid into hydroperoxyeicosatetraenoic acids (HPETEs) and their stable products hydroxyeicostetraenoic acids (HETES). Lipoxygenases are classified according to the position in the arachidonic acid which is oxygenated. Platelets metabolize arachidonic acid to 12-HETE, while polymorphonuclear leukocytes contain 5 and 15 lipoxygenases. It is known that 12-HETE and 4,12-diHETE are chemotactic for human neutrophils and eosinophils, and may augment the inflammation process, 5-HPETE is known to be a precursor of slow-reacting substance of anaphylaxis (SRS-A). The SRS family of molecules, such leukotrienes B, C, and D, have been shown to be potent bronchoconstrictors (see, NATURE 288, 484–486 (1980).

Protocol 1 describes an assay to detect inhibitors of the lipoxygenase pathway. Such inhibitors are believed to be capable of modulating the biosynthesis of the leukotrienes, a property believed to be useful in treating asthma and inflammatory disease states.

PROTOCOL 1

A suspension of rat neutrophils in buffer is incubated for 3 minutes at 30° C. with [$^{14}$C]-arachidonic acid (AA) and Calcium Ionophore A23187. Citric acid (2M) is used to quench the reaction. Following the addition of a trace amount of ($^3$H)-5-HETE together with an excess of unlabeled 5-HETE to each tube, the mixture is extracted with chloroform/methanol. The organic layer is washed with dilute acid and an aliquot is transferred to glass tubes and dried. The residue is dissolved in a small volume of chloroform and an aliquot is spoted on silica gel TLC sheets, which are developed with an ethyl acetate/isooctane/water acetic acid solvent system. The 5-HETE spots are visulaized with iodine, cut out and placed in scintillation vials for counting. After adjusting for the extraction efficiency, the amount (pmole) of [$^{14}$C]-5-HETE in each of the tubes is quantitated. The net pmoles of 5-HETE are obtained by subtracting the pmoles of 5-HETE in the tubes containing buffer alone (blank) from the pmoles of 5-HETE in the tubes containing buffer and cells (control). The ability of the test compounds to modulate the activity of this enzyme is determined by a decrease or increase in the net amount of 5-HETE produced.

Table I shows the concentration required for inhibition of the 5-lipoxygenase pathway (5-Lox/I$_{50}\mu$m) for compounds of the present invention.

TABLE I

| Inhibition of 5-Lipoxygenase | |
|---|---|
| Compound of Example | Lox, Rat PMN(I$_{50}$ μm) |
| 1 | 56 |
| 2 | 55 |
| 3 | 2.3 |
| all trans retinoic acid | 90.0 |
| Ro 10 - 9359 } Standard | 10 ± 17% |
| Ro 11 - 1430 | −11 ± 19% |

Compounds of this invention also display potent activities in regulating phosphilipases and as such possesses therapeutic value in the treatment of inflammatory conditions.

Inflammatory responses to a variety of offending stimuli are promoted by products of arachidonic acid metabolism. These products include leukotrienes (SRS-A), prostaglandins, prostacyclin and its metabolites, and thromboxanes. No matter what combination of products results from passage of substrate down the branches of this complex cascade, the initial step involves the release of arachidonic acid from phospholipids or from triglycerides containing this long-chain fatty-acid. The enzymes catalyzing such release of arachidonic acid are:

(a) phospholipase C followed by diglyceride lipase;

(b) phospholipase A$_2$, either soluble or membrane-bound; and (c) a lipase able to degrade triglycerides that contain arachidonic acid.

An assay has been developed to test the ability of the invented compounds on the activity of the phospholipases. The following protocol describes a means for testing the inhibitory effect of these compounds on Phospholipase A$_2$ (PLA$_2$).

PROTOCOL II

In Vitro Assay for Inhibitors of Phospholipase A$_2$ Assayed at pH 7.0 (PLA$_2$)

The PLA$_2$ employed in this screen is obtained by aggregation of purified rat platelets. In the enzyme assay phosphatidylcholine having $^{14}$C-labeled palmitate residues at R$_1$ and R$_2$ is employed as substrate. PLA$_2$ acts by cleaving the R$_2$ fatty acid ester bond yielding free fatty acid and lysophosphatidylcholine as follows:

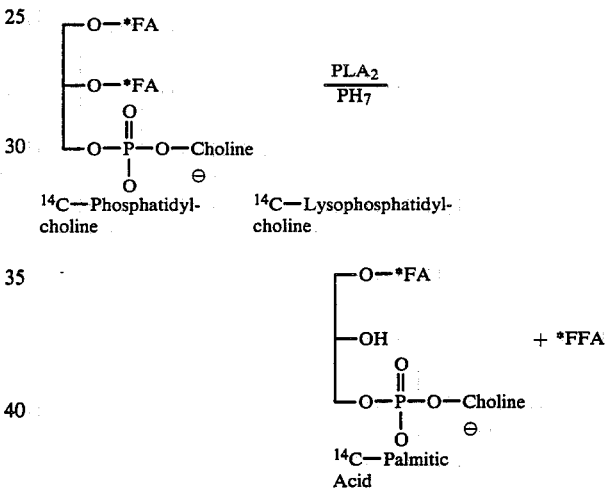

Following completion of the reaction, the assay medium is acidified and extracted with hexane, which takes up unreacted substrate and free fatty acid product. The hexane extract is passed over a short silica column which retains 99% of the phosphatidylcholine. The $^{14}$C-labeled palmitic acid is not retained (90% recovery in eluate) and is collected directly in scintillation counting vials. The released palmitic acid is conveniently quantitated by liquid scintillation spectrometry.

The compounds were tested at 100 μM in a buffer containing 0.3 mM unlabeled phosphatidylcholine (PC), 20–30,000 cpm of $^{14}$C(CPC), 100 μM NaCl, 1 mM CaCl$_2$ and 50 mM tris-HCl adjusted to pH 7.2 with 1N NaOH. This resulted in a buffer at pH 7.2. The temperature of the buffer was maintained at a temperature of 37° C. The reaction was initiated by addition of the enzyme and it was terminated 30 minutes later by the addition of 100 ml of 1N HCl.

Following acidification, the samples were extracted with 2 ml of 2-propanol and 2 ml of hexane, vortexed and allowed to stand until the phases separated. Free fatty acids (FFA) and some unreacted substrate were taken up in the isopropanol-saturated hexane. The hexane phase of the extraction mixture was transferred to a short silica gell column which retained reacted PC but not the FFA. The column effluent was collected directly in scintillation vials. The columns were washed once with an additional 2 ml of hexane. The radio labeled FFA were quantitated by liquid scintillation spectrometry.

The result is shown in Table II.

TABLE II

| PHOSPHOLIPASE $A_2$ INHIBITION (Rat Platelets) | |
|---|---|
| Compound of Example | Activity ($I_{50}$) or % Inhibition |
| 1 | 56 μM |
| 2 | 48 μM |
| 3 | 34 μM |
| 4 | 17 μM |
| all trans-retinoic acid (standard) | 32% I at 100 μM |

The therapeutic agents of this invention may be administered alone or in combination with pharmaceutically-acceptable carriers, the proportion of which is determined by the solubility and chemical nature of the compound, chosen route of administration and standard pharmaceutical practice. For example, they may be administered orally in the form of tablets or capsules containing such excipients as starch, milk, sugar, certain types of clay and so forth. They may be administered orally in the form of solutions which may contain coloring and flavoring agents or they may be injected parenterally, that is intramuscularly, intravenously or subcutaneously. For parenteral administration, they may be used in the form of a sterile solution containing other solutes, for example, enough saline or glucose to make the solution isotonic. When applied topically for treating skin disorders, the present new products can be provided in the form of dusting powders, aerosol sprays, ointments, aqueous compositions including solutions and suspensions, cream lotions and the like. In this regard, any of the commonly employed extending agents can be used depending on the nature of the product as is well-known in the art.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity give parenterally.

What is claimed is:

1. A method for treating inflammatory conditions and allergic responses in a human host which comprises administering to said host a therapeutically effective amount of at least one compound of the formula

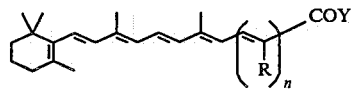

where
R=H or an alkyl group of from 1 to 5 carbon atoms

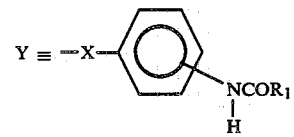

n=0-1
X=O or S; and
$R_1$=an alkyl group of from 1 to 5 carbon atoms; and the pharmaceutically acceptable salts thereof.

2. A therapeutic composition for the treatment of inflammatory conditions and allergic responses in a human host, in combination with at least one pharmaceutically acceptable extender, a therapeutically effective amount of a compound of the formula

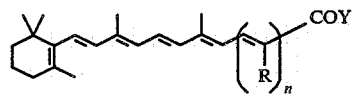

where
R=H or an alkyl group of from 1 to 5 carbon atoms

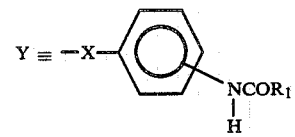

n=0-1
X=O or S; and
$R_1$=an alkyl group of from 1 to 5 carbon atoms; and the pharmaceutically acceptable salts thereof.

* * * * *